(12) United States Patent
Vernickel et al.

(10) Patent No.: US 7,777,492 B2
(45) Date of Patent: Aug. 17, 2010

(54) MAGNETIC RESONANCE COMPATIBLE DEVICE AND A METHOD OF CONDUCTING A HIGH FREQUENCY POWER SIGNAL BETWEEN REGIONS OF THE DEVICE

(75) Inventors: Peter Vernickel, Hamburg (DE); Bernhard Gleich, Hamburg (DE); Kai-Michael Luedeke, Halstenbek (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 296 days.

(21) Appl. No.: 11/908,810

(22) PCT Filed: Mar. 31, 2006

(86) PCT No.: PCT/IB2006/050975

§ 371 (c)(1),
(2), (4) Date: Sep. 17, 2007

(87) PCT Pub. No.: WO2006/103635

PCT Pub. Date: Oct. 5, 2006

(65) Prior Publication Data

US 2008/0143459 A1 Jun. 19, 2008

(30) Foreign Application Priority Data

Apr. 1, 2005 (EP) .................................. 05102590

(51) Int. Cl.
*G01V 3/00* (2006.01)
*A61B 5/05* (2006.01)
(52) U.S. Cl. ...................... 324/322; 324/318; 324/307; 600/411; 600/422; 600/435
(58) Field of Classification Search ......... 324/300–322; 600/407–435, 330; 330/141, 126; 333/24 C, 333/219, 219.2
See application file for complete search history.

(56) References Cited

U.S. PATENT DOCUMENTS 3,081,428 A * 3/1963 Fowler ........................ 324/322

(Continued)

FOREIGN PATENT DOCUMENTS

WO 2004038442 A2 5/2004
WO 2004090914 A1 10/2004

OTHER PUBLICATIONS

Ferhanoglu, O., et al.; Investigating RF heating of pacemakers in MRI using a safety index; 2004; Proc. Intl. Soc. Mag. Reson. Med.; 11:662.
Ladd, M. E., et al.; Reduction of Resonant RF Heating in Intravascular Catheters Using Coaxial Chokes; 2000; MRM; 43:615-619.

*Primary Examiner*—Brij B. Shrivastav
*Assistant Examiner*—Tiffany A Fetzner (57) ABSTRACT

The arrangement (10) is suited for transmitting an informative signal (S1), generated by suitable signal generator (1) at a first electrical site (7a) to a second electrical site (7b). The first electrical site (7a) is electrically connected to the second electrical site (7b) by means of a capacitively coupled transmission line (5a, 5b). In order to enable such capacitively coupled transmission line distributed or lumped capacitors (4a, 4b, 4c, 4d) can be used. The arrangement is connectable to an accessory device (6), which may comprise a spectrometer, a further signal generator, tuning means, etc. The further signal (S2) is generated by the accessory device (6) and transported via the capacitively coupled transmission line (5a, 5b) in a direction from the second electrical site (7b) to the first electrical site (7a). The further signal (S2) can be used for feeding an amplifier (2), or for carrying the signal (S1). The arrangement further relates to a magnetic resonance compatible device, a magnetic resonance imaging system and a method of sensing magnetic resonance energy.

13 Claims, 5 Drawing Sheets

U.S. PATENT DOCUMENTS

| | | | | |
|---|---|---|---|---|
| 3,113,263 | A * | 12/1963 | Collins | 324/316 |
| 3,169,225 | A * | 2/1965 | Okwit | 330/4.6 |
| 4,672,972 | A | 6/1987 | Berke | |
| 5,964,705 | A | 10/1999 | Truwit et al. | |
| 6,236,205 | B1 | 5/2001 | Ludeke et al. | |
| 6,263,229 | B1 | 7/2001 | Atalar et al. | |
| 6,447,448 | B1 * | 9/2002 | Ishikawa et al. | 600/300 |
| 6,586,994 | B2 * | 7/2003 | Pomata et al. | 330/141 |
| 7,202,734 | B1 * | 4/2007 | Raab | 330/126 |
| 2002/0175752 | A1 * | 11/2002 | Pomata et al. | 330/141 |
| 2003/0173966 | A1 | 9/2003 | Scott et al. | |
| 2003/0203717 | A1 * | 10/2003 | Chuprun et al. | 455/12.1 |
| 2003/0227289 | A1 | 12/2003 | Heid et al. | |
| 2004/0056103 | A1 * | 3/2004 | Sepponen | 235/487 |
| 2007/0229079 | A1 * | 10/2007 | Vernickel et al. | 324/322 |
| 2008/0143459 | A1 * | 6/2008 | Vernickel et al. | 333/24 C |

* cited by examiner

MAGNETIC RESONANCE COMPATIBLE DEVICE AND A METHOD OF CONDUCTING A HIGH FREQUENCY POWER SIGNAL BETWEEN REGIONS OF THE DEVICE

FIELD OF THE INVENTION

The invention relates to an arrangement comprising an electronic circuit.

The invention further relates to a magnetic resonance compatible device.

The invention still further relates to a magnetic resonance imaging system.

The invention still further relates to a method of conducting a signal.

BACKGROUND OF THE INVENTION

An embodiment of the arrangement as is set forth in the opening paragraph is known from U.S. Pat. No. 4,672,972. The known arrangement is used to detect nuclear magnetic resonance spectra from an object subjected to a magnetic resonance excitation. For this purpose in the known arrangement the generator comprises a receiving coil which is arranged to generate the informative signal by picking up a free induction decay signal generated in the object at Larmor frequency. In order to transmit the informative signal from the first electrical site, notably the measurement site, to the second electrical site, notably a data analysis site, the known arrangement comprises a wiring cable whereto a suitable amplifier is connected for amplification of the informative signal.

It is a disadvantage of the known arrangement that the electrical field generated by the radio-frequency operatable receiver coil induces radio-frequency currents in the wiring, which may be hazardously increased due to the fact that the wiring and the surrounding medium can form a resonant circuit. The thus induced currents induce not only parasitic disturbances of suitable accessory devices, but may lead to a substantial heating of the wiring and the surrounding medium, which is unacceptable, especially when such arrangement are conceived to be applied in-vivo. It is noted that in principle an imaging session comprises two phases: "transmit" and "receive". In the transmit phase all receivers are detuned and normally do not produce hazardous signal. The wiring, on the contrary, being a conductor constitutes a receiver in which hazardous currents are induced and may be amplified by a cable resonance.

It is an object of the invention to provide an arrangement which is substantially compatible to a radio-frequency environment, notably the magnetic resonance imaging environment.

SUMMARY OF THE INVENTION

The arrangement according to the invention.

The technical measure of the invention is based on the insight that by sub-dividing a continuous wiring line into a plurality of portions comprising elements with capacitive electrical properties, hazardous common mode radio-frequency resonances, notably at Larmor frequency are avoided on one hand, and by provision of a signal generating circuit an architecture of the electrical circuit can be simplified substantially. The capacitively coupled transmission line may be designed to have a substantial impedance of respective capacitive couplers for common mode. This also results in an attenuation for the informative signal, which may be generated at the first electrical site. To compensate for the attenuation of the informative signal the arrangement according to the invention comprises the amplifier, preferably located in the thus formed electrical circuit nearby the first electrical site. It is noted that the capacitively coupled transmission line is known per se from WO 2004/090914 A1. The disadvantage of the known capacitively coupled transmission line is in the fact that the informative signal is substantially attenuated while passing through the known capacitively coupled transmission line, leading to a poor signal/noise ratio of the informative signal at the second electrical site. This disadvantage is solved by the arrangement according to the invention by providing an amplifier for suitable amplification of the informative signal.

In the arrangement according to the invention, the arrangement further comprises a further generator for generating a further signal conceived to be transmitted via said wiring at least in a direction from the second electrical site to the first electrical site, whereby the transmission line is further arranged to have a passband for the further signal.

It is found to be advantageous to provide a further signal in the wiring, which may be conveniently used as a carrier signal for the informative signal. Thus, the informative signal is advantageously converted to another frequency with a lower attenuation in the wiring. Alternatively, the further signal may be used as a feed signal for the amplifier of the arrangement. It is preferable to select a higher frequency for the further signal than the frequency of the informative signal, because the impedance of the capacitively coupled transmission line decreases with frequency.

In addition, in the arrangement according to the invention the amplifier is further arranged to comprise a device actuatable by the further signal for multiplying the informative signal.

Due to this feature, extra electronic circuitry for rectifying/storing/smoothing/stabilizing the radio-frequency power of the further signal sent to direct current supply of the amplifier is omitted resulting in a simpler arrangement of electric circuitry. The amplifier is thus arranged to comprise a device, for example a transistor array, that can be directly driven by radio-frequency signals of the magnitude of usual supply voltage/currents levels. The gain of such amplifier is a function of the momentary drive level, leading to a resulting output signal being not only an amplified signal, but also a mixer or frequency translation function providing sum and difference frequencies. Preferably, a diplexer is arranged in the electrical circuit of the arrangement according to the invention, for splitting or combining these different output signal components optimally in the required way. Further details of the present embodiment are discussed with reference to FIG. 3.

In an embodiment of the arrangement according to the invention, the capacitive couplers comprise electric lumped capacitors or electric distributed capacitors. The distributed capacitors may be formed by electrical conductors aligned in mutual close vicinity and separated by a suitable dielectric material.

It is found to be advantageous to use electric distributed capacitors as they enable a design of the capacitively coupled transmission line and may be miniaturized. The latter feature is particularly important for interventional devices, like catheters, probes, implants, notably pacemakers.

In a still further embodiment of the invention the amplifier comprises a parametric amplifier.

It is found to be advantageous to use a parametric amplifier based on non-linear properties of components in the arrangement according to the invention. Examples of suitable parametric amplifiers comprise a varactor diode, or a capacitor with non-linear permittivity. An example of the arrangement using a varactor diode will be explained with reference to FIG. 1. Preferably, the bias point of the diode is adjustable by supplying short RF pulses from the second electrical site. The RF pulses will be rectified by a suitable additional diode or the varactor diode itself and may be smoothed using an optional capacitor. Conveniently this feature offers an option to tune a resonant frequency of the signal generator when it is implemented as a LC-resonant circuit.

The parametric amplifier operates using a high frequency further signal because achievable amplification is directly related to the ratio between the frequency of the further signal and the frequency of the informative signal. The amplified signal is also at a high frequency because it is usually taken at a difference frequency of the further signal and the informative signal.

In a still further embodiment of the invention, whereby the further signal comprises a radio-frequency signal and the amplifier comprises a linear amplifier, the arrangement further comprises a converter arranged in an electrical connection with the linear amplifier for extracting a direct current component from the further signal for feeding the linear amplifier.

In a still further embodiment of the arrangement according to the invention, a conventional linear amplifier is used. The direct current to drive the amplifier is obtained by sending radio-frequency power by means of the further signal at a convenient frequency and by converting it to direct current at the amplifier's location using a suitable converter. In this arrangement the convenient frequency is freely selectable so that the further signal does not disturb the informative signal or the accessory devices conceived to be connected to the arrangement according to the invention. Further details of this embodiment are discussed with reference to FIG. 2.

The magnetic resonance compatible device according to the invention is arranged to comprise the arrangement as is discussed in the foregoing.

It is found to be particularly advantageous to provide a magnetic resonance compatible device, notably a magnetic resonance compatible interventional device like a catheter or an external device, which is safe with respect to induced currents even in the environment of magnetic resonance imaging. Preferably, the envisaged devices are used for high-frequency ablation procedures, invasive temperature or pressure sensors, nuclear magnetic resonance probes used for tracking, etc. Still preferably, when the device is an interventional device which is catheter-based, the first electrical site is located at the distal end (tip) of the catheter for picking up the informative signal. In case the amplifier is designed based on a varactor diode, it is preferable that only the varactor diode is located at the distal end of the catheter, whereby other electronic components of the thus formed parametric amplifier are placed at a proximal end of the catheter. Further details of the magnetic resonance compatible device according to the invention are discussed with reference to FIG. 4. Still preferably, the magnetic resonance compatible device comprises a pacemaker. It is found to be advantageous to design a pacemaker, which is safe with respect to induced currents even in environments with high intensity radio-frequency signals, notably in the environment of magnetic resonance imaging.

The magnetic resonance imaging system according to the invention.

It is found to be advantageous to provide a fully integrated system for magnetic resonance imaging, whereby the magnetic resonance compatible device, notably an interventional catheter is used for accurate tracking without inducing hazardous currents in the accessory devices or without heating the environment, notably the patient being imaged. Further aspects of the magnetic imaging system according to the invention will be discussed in more detail with reference to FIG. 5.

BRIEF DESCRIPTION OF THE DRAWINGS

These and other aspects of the invention will be discussed in more detail with reference to figures.

DETAILED DESCRIPTION OF THE EMBODIMENTS

Figure 1:
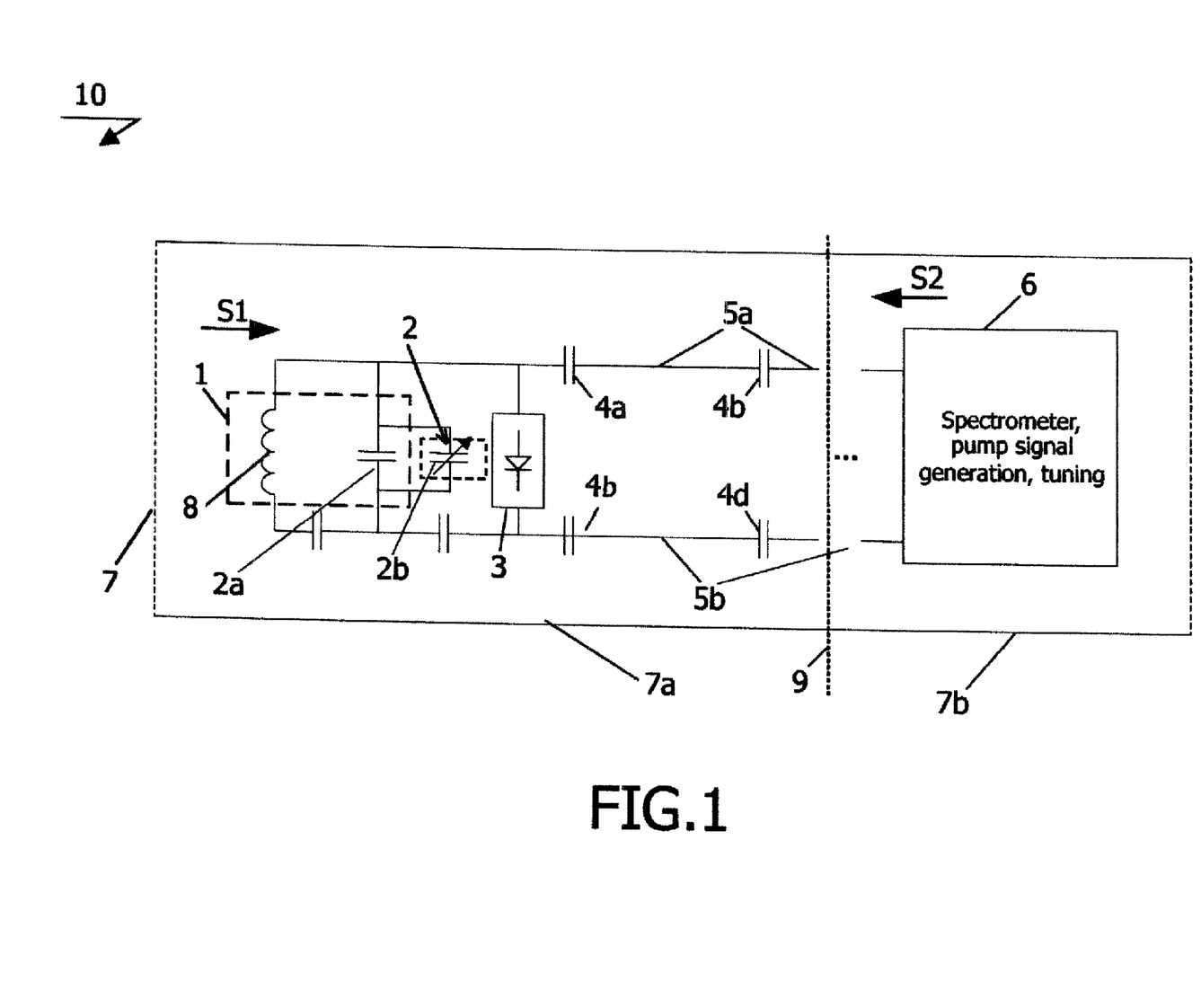
FIG. 1 presents a schematic view of an embodiment of the arrangement according to the invention using a parametric amplifier.

FIG. 1 presents a schematic view of an embodiment of the arrangement according to the invention using a parametric amplifier. Embodiments of suitable parametric amplifiers based on nonlinear properties of components comprise, for example, electric capacitance of the varactor diode or a capacitor with non-linear permittivity. The arrangement 10 according to the invention is suited for transmitting an informative signal S1, generated by suitable signal generator 1 at a first electrical site 7a to a second electrical site 7b. The first electrical site 7a is electrically connected to the second electrical site 7b by means of a capacitively coupled transmission line 5a, 5b. In order to enable such capacitively coupled transmission line distributed or lumped capacitors 4a, 4b, 4c, 4d can be used. The arrangement is connectable to an accessory device 6, which may comprise a spectrometer, a further signal generator, tuning means, etc. The further signal S2 is conceived to be generated by the accessory device 6 and to be transported via the capacitively coupled transmission line 5a, 5b in a direction from the second electrical site 7b to the first electrical site 7a. The further signal S2 can be used for feeding the amplifier 2, or for carrying the signal S1.

The present embodiment will describe the arrangement according to the invention based on a voltage dependent capacitor 2b. It is noted that the principle of the voltage dependent capacitor is known per se in the art, whereby for all elements thereof standard technology may be used. The principle of the amplification by parametric amplifier can be explained as follows: the capacitance C of a capacitor is determined by the charge Q and the voltage V: $C=Q/V$. If the charge is kept constant and of capacitor 2a is decreased, the voltage increases. This can be understood as amplification of the voltage V. The change of the capacitance of the capacitor 2a can be obtained by using a voltage dependent capacitor 2b. Parametric amplifiers are low noise amplifiers and their power amplification is limited to about 20 dB, which is directly related to a ratio of a frequency of the further signal S2 and the informative signal S1 and the power of the further signal S2. Additionally, the arrangement 10 may comprise a varactor diode or other bias setting device 3. The further signal S2 is preferably selected in the order of about ten times of the frequency of the informative signal S1. Preferably, the portions of the capacitively coupled transmission line 5a, 5b are selected to be short compared with the wavelength.

Preferably, the arrangement 10 according to the invention is accommodated in a magnetic resonance compatible device, notably a catheter 7 used for MR-tracking, MR-measuring, or for conducting a therapeutic handling under MR supervision. Thus, the first electrical site 7a is located in the distal portion of the catheter (the tip), whereas the second electrical site is located at the proximal portion of the catheter 7, which are separated by an imaginary line 9. In order to generate the informative signal S1 representative of a suitable MR measurement, the signal generator 1 comprises a resonant circuit, comprising a receive coil 8 and the capacitor 2a. The voltage dependent capacitor 2b, connected in parallel to the capacitor 2a serves for amplification of the informative signal S1. The bias point of the voltage dependent capacitor 2b can be adjusted with short RF pulses rectified by a suitable additional diode or the voltage dependent capacitor itself and smoothed by an optional capacitor. This option advantageously enables a suitable tuning of the resonant frequency of the receive coil.

Figure 2:
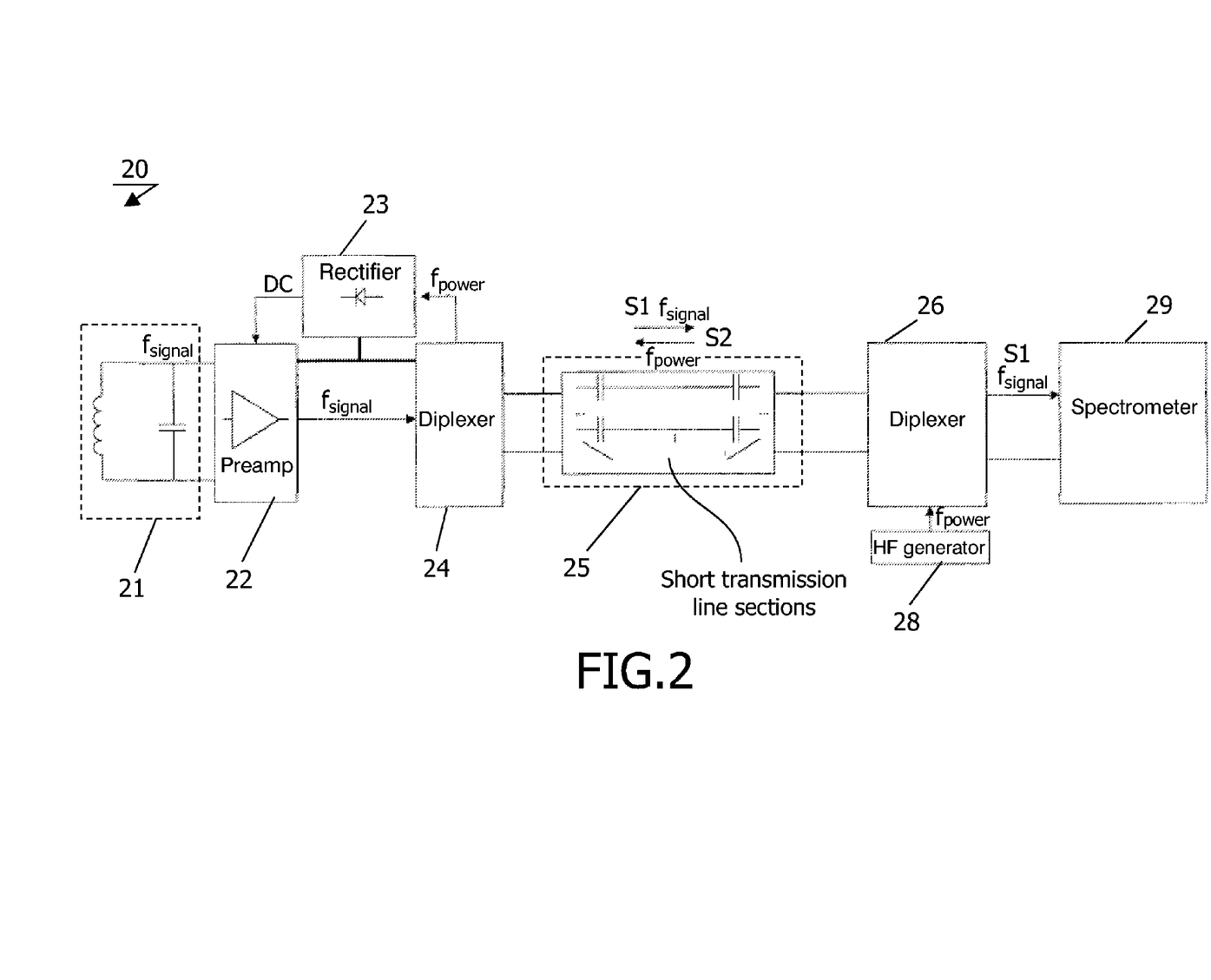
FIG. 2 presents a schematic view of an embodiment of the arrangement according to the invention with an amplifier fed by the rectified RF signal.

FIG. 2 presents a schematic view of an embodiment of the arrangement 20 according to the invention with an amplifier is fed by the further RF signal. The arrangement 20 comprises a linear pre-amplifier 22. The informative alternating signal S1 is generated by the signal generator 21, and is amplified by the linear pre-amplifier 22. The linear pre-amplifier 22 is fed by the further signal S2, which is provided by a high frequency generator 28, located at or beyond the second electrical site. The further signal is fed by the capacitively coupled transmission line 25 via the rectifier 23 to the linear pre-amplifier 22. The diplexers 24 and 26 separate or join the different RF signals as required. Optionally an accessory device 29, such as a spectrometer, is used in the arrangement 10 for carrying out a suitable data analysis.

Figure 3:
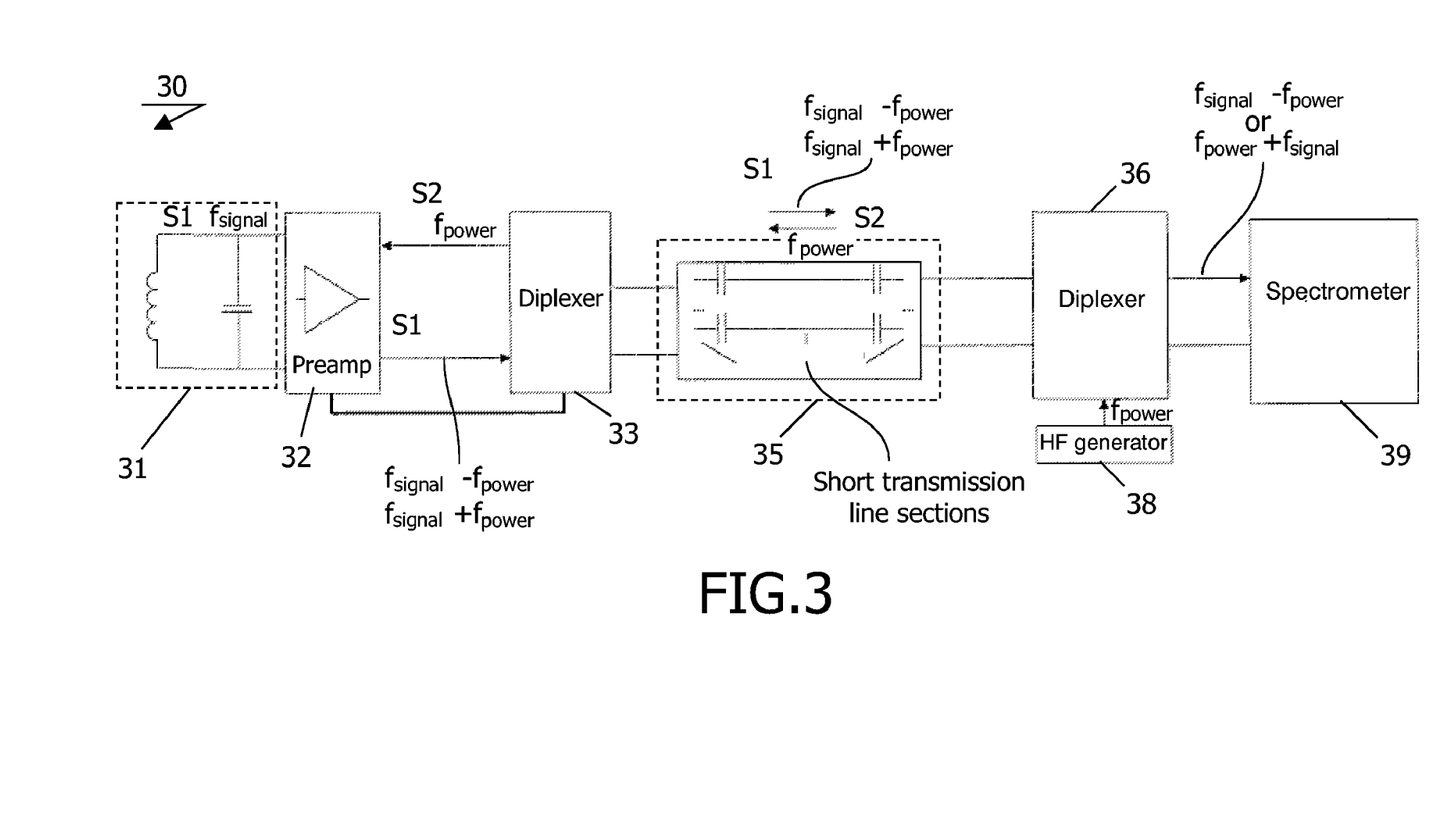
FIG. 3 presents a schematic view of an embodiment of the arrangement according to the invention with a mixer fed by the further RF signal.

FIG. 3 presents a schematic view of an embodiment of the arrangement according to the invention with a mixer fed by the further RF signal. This particular embodiment removes the necessity for an extra electronic circuitry for rectifying/storing/smoothing/stabilizing of the RF power sent by means of the further signal 52 to the DC supply of the linear amplifier, as discussed with reference to FIG. 2. The amplifier of the present embodiment of the arrangement 30 comprises an amplification device 32, for example a transistor array, that can be directly driven by the RF signal of the magnitude of usual supply voltage/currents levels of the high frequency signal generator 38. The gain of such amplification device 32 is a function of the momentary drive level. The result of the amplification will also comprise a mixing of frequency or frequency translation function providing sum or difference frequencies between the informative signal S1 from the signal generator 31 and the further signal S2. The diplexers 33 and 36 are preferably designed to split or to combine different signal components carried on the capacitively coupled transmission line 35 in the required way. The amplified mixed or translated informative signal 51 is preferably supplied to the spectrometer 39 for data analysis.

Figure 4:
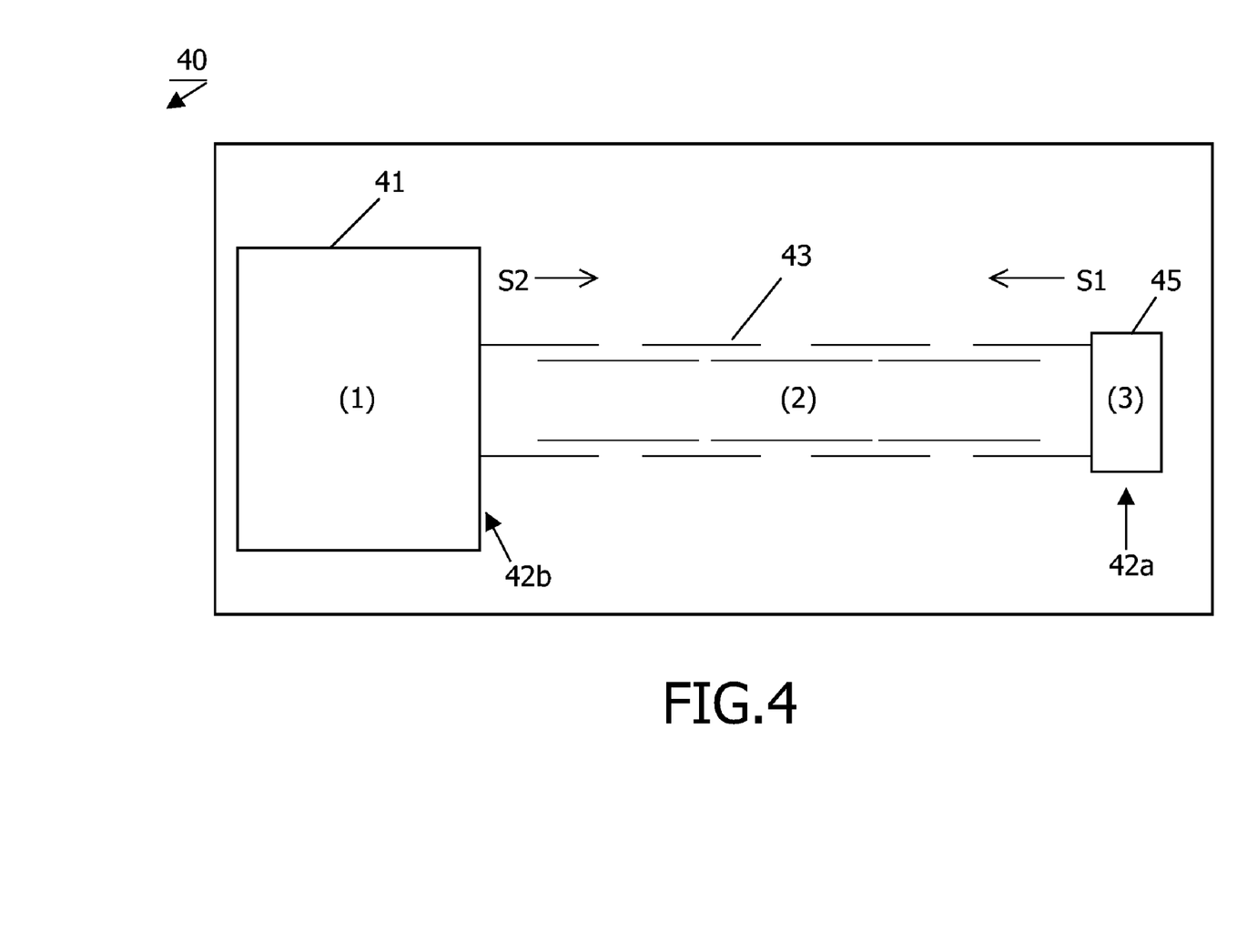
FIG. 4 presents a schematic view of a first embodiment of the magnetic resonance compatible device according to the invention.

FIG. 4 presents a schematic view of a first embodiment of the magnetic resonance compatible device according to the invention. The magnetic resonance compatible device 40 may be implemented as an implantable pacemaker. In this case, the informative signal S1 is generated by suitable signal generation means 45 located at the first electrical site 42a, said signal S1 being representative of cardiac activity of the recipient. The informative signal is amplified by suitable amplification means (not shown) in accordance with the principles described in the foregoing. The amplified signal is transmitted via the capacitively coupled transmission line 43 to the second electrical site 42b, where it is being analyzed by suitable per se known data analysis means 41. In case when the measured cardiac activity deviates from the usual pattern of the recipient a suitable correction signal is sent to the electrodes of the pacemaker (not shown) to correct the heart rhythm. This embodiment of the pacemaker is particularly suitable for undisturbed performance in environments with high intensity of radio-frequency radiation, in particular in the environment of magnetic resonance imaging.

Figure 5:
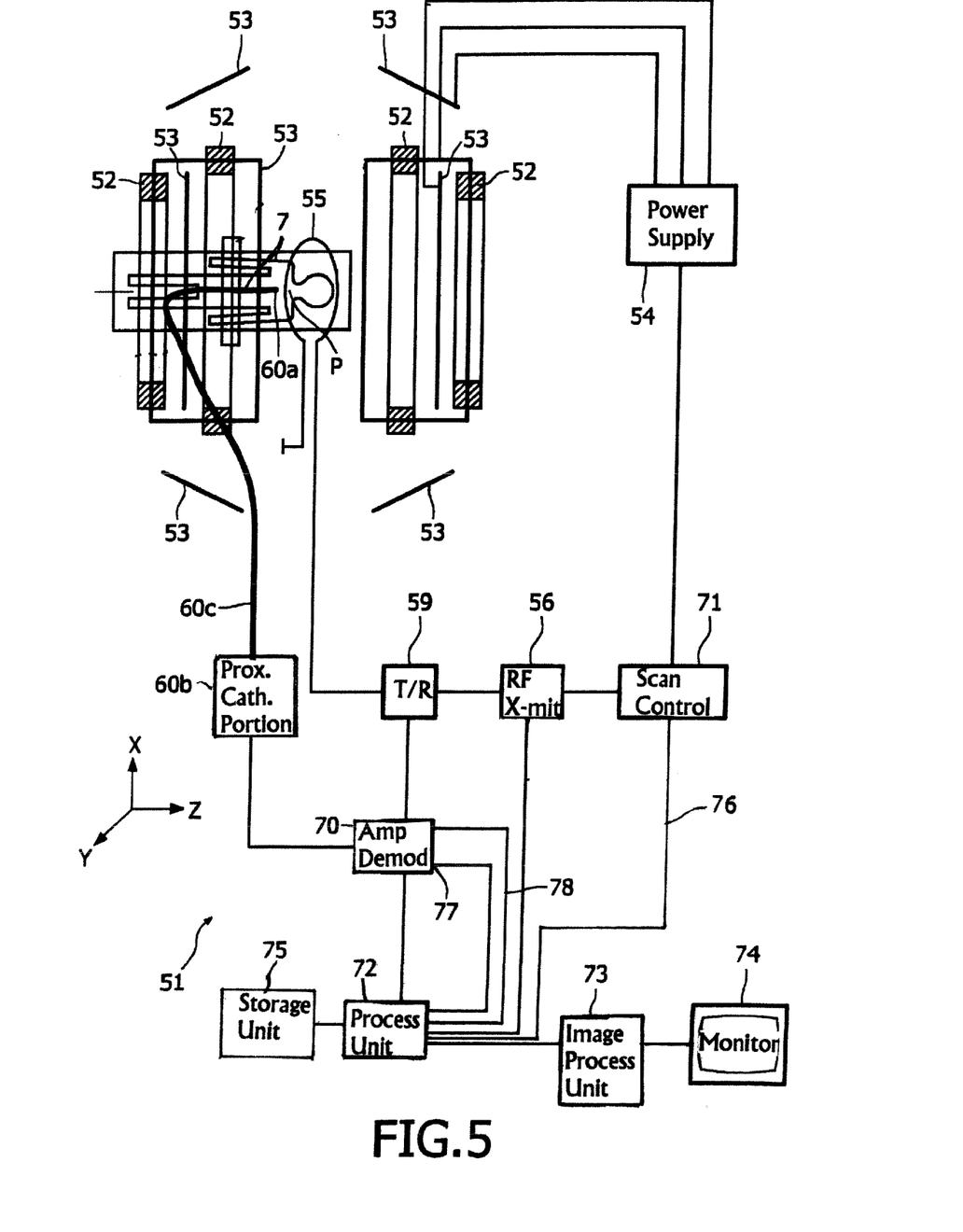
FIG. 5 presents a schematic view of the magnetic resonance imaging system according to the invention.

FIG. 5 presents a schematic view of the magnetic resonance imaging system 51 according to the invention. The magnetic resonance imaging system 51 comprises a first magnet system 52, a second magnet system 53, a power supply unit 54, an RF transmitter and modulator 56, an RF transmitter coil 55, a transmitter-receiver circuit 59, a signal amplifier and demodulation unit 70, a processing unit 72, an image processing unit 73, a monitor 74, and a control unit 71. The first magnet system 52 serves to generate a steady magnetic field B0 in an imaging volume (not shown) of the magnetic resonance imaging system 51. The various gradient coils of the second magnet system 53 serve to generate additional magnetic fields having a gradient in the X, Y, Z directions, respectively. The Z direction of the coordinate system shown in FIG. 5 corresponds by convention to the direction of the steady magnetic field in the magnet system 52. The measuring coordinate system x,y,z to be used may be chosen independently of the X, Y, Z system illustrated in FIG. 5. In the context of the present application gradients are to be understood to mean temporary magnetic fields which are superposed on a steady magnetic field and cause a gradient in the steady magnetic field B0 in three respective orthogonal directions.

The gradient coils 53 are fed by the power supply unit 54. The RF transmitter coil 55 serves to generate RF magnetic fields and is connected to the RF transmitter and modulator 56. The transmitter coil 55 is connected to the signal amplifier and demodulator unit 70 via the transmitter-receiver circuit 59. The control unit 71 controls the RF transmitter and modulator 56, the power supply unit 54.

The magnetic resonance imaging system 51 further comprises a magnetic resonance compatible device, notably an interventional catheter 7, which is conceived to be introduced in a vicinity of a target volume (not shown) of the patient P for diagnostic or therapeutic purposes. The distal portion 60a of the catheter comprises a signal generation means (not shown) for generation the informative signal, which is amplified accordingly. The amplified informative signal is transmitted via the capacitively coupled transmission line 60c to the proximal portion 60b of the catheter. The proximal portion 60b is connected to suitable accessory devices which are arranged to carry out data analysis. Preferably, the accessory devices are connected to scan controls 71 and processing unit 72 by means of wiring 77, 78, whereby the control of the transmit and receive coils of the scanner is enabled in accordance with the signal generated in the catheter 7. Preferably, the magnetic resonance imaging system 50 further comprises a storage unit 75 for storing suitable data and a display unit 74 for displaying suitable diagnostic data, like anatomic structures of the target volume and further information related to the signal of the catheter 7.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A magnetic resonance compatible interventional device configured for use in a magnetic resonance device that operates with a selected resonance frequency comprising
   a signal generating unit arranged in a first region of the interventional device which generates a radio frequency signal at the selected resonance frequency;
   a capacitively coupled signal transmission line arranged between said first region and a second region of the interventional device including a plurality of alternating conductive segments and capacitors tuned to have a high impedance at the selected resonance frequency in order to suppress common mode signals, the transmission line attenuating the radio frequency signals from the signal generating unit;
   a high frequency power signal generating unit which generates a high frequency power signal with a frequency higher than the radiofrequency signal from the signal generating unit, the high frequency power generating unit being disposed in the second region and connected with the capacitively coupled transmission line in order to send high frequency power signals in a direction from the second region to the first region, the transmission line being tuned to have a lower impedance at the frequency of the high frequency power signal; and
   an amplifier disposed in the first region and connected with the signal generating unit and the capacitive coupled transmission line such that the amplifier is powered by the high frequency power signal and amplifies the radio frequency signal from the signal generating unit in order to compensate for attenuation caused by the high impedance of the capacitively coupled transmission line at the frequency of the radio frequency signal from the signal generating unit.

2. The magnetic resonance compatible device according to claim 1, wherein the amplifier comprises a parametric amplifier which amplifies the radio frequency signal from the signal generating unit with an amplification based on a ratio between the frequency of the high frequency power signal and the frequency of the radio frequency signal from the signal generating unit.

3. The magnetic resonance compatible device according to claim 2, wherein the parametric amplifier includes a varactor diode with an adjustable bias point which is adjusted by the high frequency power signal propagating from the second region.

4. The magnetic resonance compatible device according to claim 1, wherein the amplifier comprises a linear amplifier, and further including:
   a converter in an electrical connection with the linear amplifier which extracts a direct current component from the high frequency power signal for feeding the linear amplifier.

5. The magnetic resonance compatible device according to claim 2, wherein the frequency of the high frequency power signal is at least 10 times the frequency of the radio frequency signal from the signal generating unit.

6. The magnetic resonance compatible device according to claim 1, wherein said device comprises a catheter with a proximal end at the second region and a distal end at the first region.

7. A magnetic resonance imaging system comprising:
   a magnetic resonance imaging device which generates magnetic resonance signals at the selected resonance frequency in an imaging volume; and
   the magnetic resonance compatible device according to claim 1.

8. The magnetic resonance compatible device according to claim 1, further including: a first diplexer disposed in the first region between the amplifier and the capacitively coupled transmission line that splits the high frequency power signal from the radio frequency signal supplied by the signal generating unit.

9. The magnetic resonance compatible device according to claim 8, further including: a second diplexer disposed in the second region between the high frequency power signal generating unit and the capacitively coupled transmission line in order to split or combine the high frequency power signal and the radio frequency signal from the signal generating unit.

10. A method of transmitting signals in a magnetic resonance device that operates with a selected resonance frequency, the method comprising:
    in a first region of an interventional device, generating a radio frequency signal with the selected resonance frequency;
    transmitting the radio frequency signal from the first region to a second region of the interventional device along a capacitively coupled signal transmission line which includes alternating conductive segments and capacitors;
    with the capacitively coupled transmission line, suppressing common mode signals by presenting a high impedance to signals at the selected resonance frequency and attenuating the radio frequency signals traveling from the first region to the second region;
    conveying high frequency power signals along the capacitively coupled transmission line from the second region to the first region, the capacitively coupled transmission line being tuned to present a low impedance to signals at the frequency of the high frequency power signals such that the high frequency power signals are conveyed to the first region with minimal attenuation;
    in the first region, powering an amplifier with the high frequency power signals; and
    with the amplifier, amplifying the radio frequency signals in order to compensate for the capacitively coupled transmission line attenuation and conveying the amplified radio frequency signals along the capacitively coupled transmission line from the first region to the second region.

11. The method according to claim 10, wherein the radio frequency signal is amplified in the first region with a parametric amplifier which amplifies the radio frequency signal based on a ratio between the frequency of the high frequency power signal and the frequency of the radio frequency signal.

12. The method according to claim 11, wherein the high frequency power signal is at least 10 times the frequency of the radio frequency signal.

13. The method according to claim 11, further including:
    transmitting resonance excitation signals at the selected resonance frequency into an imaging volume, at least a portion of the capacitively coupled signal transmission line being diposed in the imaging volume;
    inducing common mode signals in the capacitively coupled transmission line with the radio frequency excitation pulses;
    attenuating the common mode signals with the high impedance of the capacitively coupled transmission line presented to signals at the selected resonance frequency.

* * * * *